US012405256B2

(12) United States Patent
Xia et al.

(10) Patent No.: US 12,405,256 B2
(45) Date of Patent: Sep. 2, 2025

(54) CHEMICAL HYDROGEN PEROXIDE INDICATOR

(71) Applicant: Solventum Intellectual Properties Company, Maplewood, MN (US)

(72) Inventors: Wensheng Xia, Woodbury, MN (US); G. Marco Bommarito, Stillwater, MN (US); Naiyong Jing, St. Paul, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 982 days.

(21) Appl. No.: 17/594,256

(22) PCT Filed: Apr. 21, 2020

(86) PCT No.: PCT/IB2020/053776
§ 371 (c)(1),
(2) Date: Oct. 8, 2021

(87) PCT Pub. No.: WO2020/217175
PCT Pub. Date: Oct. 29, 2020

(65) Prior Publication Data
US 2022/0163496 A1   May 26, 2022

Related U.S. Application Data

(60) Provisional application No. 62/839,439, filed on Apr. 26, 2019.

(51) Int. Cl.
*B01J 23/10* (2006.01)
*B01J 35/50* (2024.01)
*G01N 31/10* (2006.01)
*G01N 31/22* (2006.01)

(52) U.S. Cl.
CPC ............ *G01N 31/228* (2013.01); *B01J 23/10* (2013.01); *B01J 35/50* (2024.01); *G01N 31/10* (2013.01)

(58) Field of Classification Search
CPC ...... G01N 31/228; G01N 31/10; G01N 21/78; B01J 23/10; B01J 35/50; B01J 35/393; B01J 37/0009; B01J 37/0219; B01J 37/0236; A61L 2202/24; A61L 2/208; A61L 2/28
See application file for complete search history.

(56) References Cited

U.S. PATENT DOCUMENTS

| | | |
|---|---|---|
| 4,643,876 A | 2/1987 | Jacobs |
| 4,756,882 A | 7/1988 | Jacobs |
| 4,956,145 A | 9/1990 | Cummings |
| 5,445,792 A | 8/1995 | Rickloff |
| 5,453,360 A | 9/1995 | Yu |
| 5,955,025 A | 9/1999 | Barrett |
| 6,790,411 B1 | 9/2004 | Read |
| 7,192,554 B2 | 3/2007 | Read |
| 2003/0194346 A1 | 10/2003 | Read |
| 2007/0054412 A1 | 3/2007 | Cregger |
| 2010/0124784 A1 | 5/2010 | Read |
| 2014/0234874 A1* | 8/2014 | Opperman ........... G01N 33/581 435/7.92 |
| 2015/0050745 A1 | 2/2015 | Karato |
| 2019/0154646 A1* | 5/2019 | Xia ........................ G01N 21/17 |

FOREIGN PATENT DOCUMENTS

| | | | |
|---|---|---|---|
| CN | 1610561 A | 4/2005 | |
| CN | 105044093 A * | 11/2015 | |
| CN | 109324040 A | 2/2019 | |
| DE | 10157551 A1 | 6/2003 | |
| DE | 102011088984 A1 * | 6/2013 | ......... C11D 11/0017 |
| EP | 1326074 A1 | 7/2003 | |
| EP | 1465671 | 10/2004 | |
| JP | H08320314 A | 12/1996 | |
| JP | 2014109523 | 6/2014 | |
| JP | 6143444 B2 * | 6/2017 | |
| WO | 0186289 W | 11/2001 | |

OTHER PUBLICATIONS

Fahimeh Charbgooa, Bio-sensing applications of cerium oxide nanoparticles: Advantages and disadvantages, Biosensors and Bioelectronics 96 (2017) 33-43, Available online Apr. 26, 2017 (Year: 2017).*
BYK USA Inc., Material Safety Data Sheet NANOBYK-3810, Version 4, Print Date Feb. 22, 2013 (Year: 2013).*
Asati, "Oxidase-like activity of polymer-coated cerium oxide nanoparticles", Angewandte Chem, 2009, vol. 121, pp. 2344-2348.
Database XP00279975, WPI Week 201443, AN 2014-L24909, 2017, Clarivate Analytics, 2 pages.
Jiao, "Well-redispersed ceria nanoparticles: Promising peroxidase mimetics for $H_2O_2$ and glucose detection", Analytical Methods, 2012, vol. 4, pp. 3261-3267.
International Search report for PCT International Application No. PCT/IB2020/053776 mailed on Sep. 18, 2020, 8 pages.

* cited by examiner

*Primary Examiner* — Maris R Kessel
*Assistant Examiner* — Valerie Simmons

(57) ABSTRACT

The disclosed hydrogen peroxide indicator includes a substrate on which is disposed an indicator composition that includes at least one of a select group of indicator compounds and a catalyst. As a result of contact with hydrogen peroxide, the indicator composition changes color, even from colorless to having a visually observable color, thereby providing an indication of the presence of hydrogen peroxide.

11 Claims, No Drawings

200
CHEMICAL HYDROGEN PEROXIDE INDICATOR

CROSS REFERENCE TO RELATED APPLICATIONS

This application is a national stage filing under 35 U.S.C. 371 of PCT/IB2020/053776, filed Apr. 21, 2020, which claims the benefit of U.S. Provisional Application No. 62/839,439, filed Apr. 26, 2019, the disclosure of which is incorporated by reference in its/their entirety herein.

TECHNICAL FIELD

This disclosure relates to materials for colorimetric detection of hydrogen peroxide vapor.

BACKGROUND

Medical instruments; particularly surgical instruments, are typically sterilized prior to use using steam or other sterilizing/disinfecting gases or liquids. A traditional sterilization process uses steam under pressure. Alternative sterilization processes use ethylene oxide or hydrogen peroxide in vapor from as the sterilant.

The use of hydrogen peroxide and other chemical vapor phase sterilization techniques typically involve operating temperatures well below those associated with steam sterilization. These "low, temperature" technologies generally operate at temperatures below about 65° C., and often below about 50° C. For hydrogen peroxide sterilization, the sterilized goods are typically available for use shortly after the completion of the sterilization cycle. This is because the decomposition products (e.g., water and oxygen) are non-toxic. The potency of the hydrogen peroxide may be augmented by the presence of electrical energy in the form of an ionizing plasma field.

Sterilization indicators are used to monitor whether a sterilization process has been performed. Sterilization indicators typically include an indicator composition, carried on a substrate, that changes color during the sterilization process. However, the change from one color to another may sometimes be difficult to discern by visual observation. Thus, there is still a need for a suitable indicator for vapor phase sterilization of an article using hydrogen peroxide.

SUMMARY

Disclosed is an indicator article for detecting hydrogen peroxide. The indicator article has a substrate and an indicator composition deposited thereon. The indicator composition comprises at least one indicator compound and at least one catalyst, wherein the catalyst is selected from the group consisting of a metal oxide, a metal sulfide, a noble metal, an alloy of noble metals, an allotrope of carbon, and combinations thereof. The indicator composition comprises an optical property. A visually detectable change in the optical property of the indicator composition is associated with a presence of hydrogen peroxide.

In another embodiment, the present disclosure includes method that includes providing an indicator article comprising a substrate and an indicator composition deposited thereon, wherein the indicator composition includes at least one indicator compound and at least one catalyst, wherein the catalyst is selected from the group consisting of a metal oxide, a metal sulfide, a noble metal, an alloy of noble metals, an allotrope of carbon, and combinations thereof, and wherein the indicator composition comprises an optical property, and further wherein a visually detectable change in the optical property of the indicator composition is associated with a presence of hydrogen peroxide, and visually detecting a change in an optical property of the indicator composition upon exposure to hydrogen peroxide vapor.

In another embodiment, the present disclosure includes an indicator composition comprising at least one indicator compound and at least one catalyst, wherein the catalyst is selected from the group consisting of a metal oxide, a metal sulfide, a noble metal, an alloy of noble metals, an allotrope of carbon, and combinations thereof, wherein the indicator composition comprises an optical property, and further wherein a visually detectable change in the optical property of the indicator composition is associated with a presence of hydrogen peroxide, and visually detecting a change in an optical property of the indicator composition upon exposure to hydrogen peroxide vapor.

In yet another embodiment, the present disclosure includes a composition comprising the reaction product of hydrogen peroxide and an indicator composition comprising at least one indicator compound; and at least one catalyst; wherein the catalyst is selected from the group consisting of a metal oxide, a metal sulfide, a noble metal, an alloy of noble metals, an allotrope of carbon, and combinations thereof; wherein the indicator composition comprises an optical property, and further wherein the reaction product has a visually detectable color.

The terms "visual detection" and "visually detectable" refer to detection by means of an unaided human eye.

The term "colorless" refers to an absence of visually detectable color.

The term "visually detectable" refers to detection by an unaided human eye.

DETAILED DESCRIPTION

The present disclosure provides a hydrogen peroxide indicator that includes a substrate on which is disposed an indicator composition that includes a catalyst and at least one indicator compound. As a result of contact with hydrogen peroxide, the indicator composition undergoes a change in optical properties, thereby providing an indication of the presence of hydrogen peroxide.

Disclosed is a system for indicating exposure to a hydrogen peroxide vapor sterilization process. The sterilant vapor typically includes hydrogen peroxide and water.

The indicator composition includes at least one component that is transformed in the presence of vaporous hydrogen peroxide such that an optical property of the indicator composition changes. The indicator composition may include one or more components that change optical properties upon contact with hydrogen peroxide, as well as other components that do not change optical properties upon contact with hydrogen peroxide. For example, the composition includes a polymeric binder to aid in applying the indicator composition to a suitable substrate.

The indicators are very useful in indicating when an article has been exposed to hydrogen peroxide in the vapor phase. The indicators offer a simple, yet effective means for indicating when a particular article has been subjected to sterilization using vaporous hydrogen peroxide.

The indicator compositions of the present disclosure undergo a change in optical properties when exposed to an atmosphere an aqueous solution containing about 60 weight percent (wt. %) hydrogen peroxide at 50° C. within an exposure phase of at least about 6 minutes and/or a change in optical properties when exposed to an atmosphere containing about 6 milligrams/liter (mg/l) to about 7 mg/l hydrogen peroxide (in an empty chamber, i.e., without articles to be sterilized) at a pressure of about $8\times10^2$ Pascals (Pa) to about $29.3\times10^2$ Pa and a temperature of about 45° C. to about 60° C. within an exposure phase of at least about 6 minutes, which are typical conditions within an empty commercial hydrogen peroxide plasma sterilizer. For use in conventional sterilizers, the indicator compositions of the present disclosure undergo a change in optical properties when exposed to an atmosphere is containing about 6 mg/l to about 22 mg/l hydrogen peroxide (in an empty chamber) at a pressure of about $8\times10^2$ Pa to about $29.3\times10^2$ Pa and a temperature of about 45° C. to about 60° C. within an exposure phase of at least about 50 minutes.

The optical properties of the indicator compositions do not significantly change upon exposure to room lighting (e.g., fluorescent lighting). The optical properties of the indicator compositions do not significantly change, for example, upon exposure to sunlight through a window for one week or room lighting for two months.

Indicator compositions of the present disclosure include at least one indicator compound. Several structural classes of indicator compounds can be considered., including aniline dyes, azo dyes, anthroquinone dyes, phthalocyanine dyes, thiazine dyes, indoxyl dyes, and the like. In embodiments, the indicator compound is colorless before exposure to hydrogen peroxide vapor. In some examples, the indicator compound is colorless as a dilute water solution. In some preferred embodiments, the indicator compound is 4,4'-diamino-2,2'-stilbenedisulfonic acid (DSSA) or 2,2'-azino-bis(3-ethylbenzothiazoline-6-sulfonic acid) diammonium salt (ABTS).

In some embodiments, concentration of the indicator compound in the indicator composition can be in a range from 0.01 wt. % to 20 wt. %, or in a range from 0.1 wt. % to 5 wt. %, or even in a range from 0.5 wt. % to 5 wt. %.

The indicator composition may exhibit a color change from a first color to a second color upon exposure to an active ingredient (or optionally a threshold level of active ingredient). The first color may be any color, which may include the absence of visible color (i.e., colorless). The second color may be sufficiently different than the first color such that a color contrast from the first color to the second color may be observed. When the indicator composition has a first color that is colorless, the first color may appear as the color of the substrate (e.g., colorless, white, etc.) underlying the indicator composition. The term "color" may encompass a number of aspects of color such as hue, lightness, saturation, and the like, where one color may be different from another color if the two colors differ in at least one aspect. For example, two colors which have the same hue and saturation but have a different lightness would be considered to be different colors. Any suitable color (e.g., red, white, black, gray, yellow, purple, etc.) may be used to produce a color contrast as long as the second color can be observed. The color contrast may change (e.g., diminish). The term "color contrast" may encompass any degree of color contrast sufficient to render a color change from the first color to the second color discernible to the observer regardless of whether the color contrast changes or is constant during the visible time. The indicator composition has a "first color" that is colorless. Indicator compositions include at least one catalyst. The catalyst serves accelerate the reaction of an indicator compound upon exposure to hydrogen peroxide. While a variety of reaction mechanisms may be envisioned for explaining the acceleration of reaction of the indicator compound with hydrogen peroxide can include any suitable reaction mechanism.

Non-limiting categories of suitable catalysts can include, for example, a metal oxide, a metal sulfide, a noble metal, an alloy of noble metals, an allotrope of carbon, and combinations of those catalysts. Metal oxides can include, for example, BiFeO, cerium (IV) oxide ($CeO_2$), CuO, $Co_3O_4$, $Fe_3O_4$, $MnO_2$, $V_2O_5$, ZnO, and the like, alone or in combinations. Metal sulfides can include, for example, CuS, FeS, and the like, alone or in combinations. Noble metals can include, for example, Au, Pt, Pd, and the like, alone or in combinations. Alloys of noble metals can include, for example, Bi—Au, Ag—Au, Ag—Pd, Ag—Pt, Pt—Ru, Pt—Ir, Pd—Pt, Pd—Au, and the like, alone or in combinations. Allotropes of carbon can include, for example, a fullerene, a graphene, and the like, alone or in combinations.

Among these various catalysts include cerium (IV) oxide as the catalyst. More preferred is cerium (IV) oxide nanoparticles. The nanoparticles preferably have a size less than 1000 nm, less than 100 nm, less than 20 nm, or even less than 5 nm. Useful cerium (IV) oxide nanoparticles can include, for example a 20 wt. % solution of 5 nm $Ce_2O$ nanoparticles water (available from Sigma Aldrich, St. Louis, MO).

Suitable concentration ranges for the catalyst in the indicator composition can include, for example, 0.0001 wt. % to 20 wt. %, or even 0.005 wt. % to 1 wt. %.

Indicator compositions can include a binder resin. A wide variety of suitable binder resins can be used. Examples include synthetic or natural polymers or resins. Suitable binder resins are those that do not interfere with the function of the indicator composition. Binder resins preferably do not degrade significantly on exposure to hydrogen peroxide. Some non-limiting examples of binder materials include cellulose acetate butyrate, cellulose acetate propionate, hydroxypropyl cellulose, nitrocellulose, urethane alkyd, epoxy, alkylated urea- and melamine-formaldehyde, polyamide, styrene butadiene, vinyl, phenolic, shellac, ethyl cellulose, methyl cellulose, acrylic, and ultraviolet and electron beam curable resins. Some examples of suitable binder resins include NEOREZ R-966 (available from DSM USA, Parsippany, NJ), Bondthane UD-420 (available from Bond Polymers International, Seabrook, NH), and self-crosslinking polymer emulsion such as NEOCRYL XK-95 (available from DSM USA, Parsippany, NJ)

A sufficient amount of binder resin is included in the compositions to provide adequate binding of the composition to a substrate, on which it is disposed, while providing the desired rate of change in optical property. In some embodiments, the indicator compositions contain a binder in an amount ranging from about 3 wt. % to about 99 wt. %, or even from about 80 wt. % to about 99 wt. %.

Indicator compositions can include a crosslinker. A variety of suitable crosslinker resins can be used. In some embodiments, the crosslinker is self-crosslinking, and can be used as a sole resin in the formulation of an indicator composition of the present disclosure. An example of a useful crosslinker includes the aziridine crosslinker PZ-28 (available from PolyAziridine LLC, Medford, NJ). In the case of light-sensitive crosslinkers, a photostabilizer compound can be added into the indicator composition.

Indicator compositions can be sufficiently soluble in water to facilitate application to a substrate. While organic solvents may be added to facilitate application to a substrate, it is preferable to use primarily water as the solvent.

The indicator composition may exhibit a change in optical property within a relatively short exposure to hydrogen peroxide. The exposure to hydrogen peroxide may be in the range from about 1 second to about 60 minutes, from about 1 second to about 20 minutes, from about 1 second to about 10 minutes, from 1 second to about 5 minutes, from about 1 second to about 2 minutes, from about 1 second to about 60 seconds, or even from about 1 second to about 10 seconds. The time required for hydrogen peroxide exposure to effect the change in optical property can be adjusted or controlled by varying the components in the indicator composition. For example, varying the concentration of the binder and/or the crosslinker may vary the hydrogen peroxide exposure time required for the change in optical property.

An indicator article can be read immediately after use. A sterilization process operator visually observing the indicator article can immediately discern a change in optical property after use of the indicator article in the sterilization process.

Whereas some other systems for detecting hydrogen peroxide in a sterilization process require an enzymatic component (for example, a peroxidase enzyme), indicator compositions of the present disclosure do not require an enzymatic component. For indicator articles of the present disclosure, an interaction of hydrogen peroxide with indicator compound and catalyst is sufficient to produce a visually observable change in an optical property of the indicator composition.

In some embodiments, indicator articles include a substrate. The substrate on which the indicator composition is disposed can be any of a wide variety. Typically, suitable substrates include polymeric materials, which may be pigmented or colorless. Examples of suitable substrates can include, for example: plastic films including polyester, polyethylene, or polystyrene films; nonwovens; synthetic paper; glass; and the like. Preferably, the substrate is stable towards hydrogen peroxide vapor. Additionally, the substrate preferentially does not absorb or retain hydrogen peroxide (to avoid false positive results in hydrogen peroxide detection). The substrate is typically selected to be either colorless, or white, to facilitate visual detection of a change in the optical property.

In one embodiment, the substrate is a poly(ethylene terephthalate). The substrate is either colorless, or white, making it easy to visually distinguish a change in the optical property. The substrate may be in the form of a strip of material (for example, a strip of material having the dimensions 2 cm by 13 cm). Optionally, the composition can be coated as a stripe over the length of the substrate strip. The substrate may also have an adhesive on the surface opposite that on which the indicator composition is disposed. In this way, the indicator may be used as a tape or label for attachment to the article to be sterilized.

The hydrogen peroxide vapor sterilization procedure used is conventional, and is disclosed in, for example, U.S. Pat. Nos. 4,756,882, 4,643,876, 4,956,145, and 5,445,792. Modalities of sterilization can include plasma treatment and ozone treatment.

Some examples of useful sterilization systems include those vaporized hydrogen peroxide sterilizers of the STERRAD brand, available from Advanced Sterilization Products (ASP) of Irvine, CA (e.g., STERRAD 100 System; STERRAD 100S System; STERRAD NX System (Standard and Advanced cycles); STERRAD NX System with ALLCLEAR Technology (Standard and Advanced cycles), STERRAD 100NX System (Standard, Flex, Express and Duo cycles); STERRAD 100NX System with ALLCLEAR Technology (Standard, Flex, Express and Duo cycles)), and those vaporized hydrogen peroxide sterilizers of the STERIS brand, available from Steris Corp. of Mentor, OH (e.g., STERIS V-PRO 1 (Lumen cycle); STERIS V-PRO 1 Plus (Lumen and Non-Lumen cycles); STERIS V-PRO maX Low Temperature Sterilization System (Lumen, Non-Lumen and Flexible cycles); STERIS V-PRO 60 Low Temperature Sterilization System (Lumen, Non-Lumen and Flexible cycles); STERIS V-PRO maX 2 Low Temperature Sterilization System (Lumen, Non-Lumen, Flexible, and Fast Non-lumen cycles)), and the TSO3 STERIZONE VP4 system (all cycles), available from TSO3 Corp. of Myrtle Beach, SC.

In general, the article to be sterilized is placed in a sterilization chamber with any of the preferred embodiments of hydrogen peroxide indicator of the invention, and a dose of hydrogen peroxide, which generally comes pre-measured, is delivered to the chamber. Vapor is generated and allowed to fill the container for an appropriate length of time after which the sterilization is complete. The indicator is then inspected for a color change. The equipment and the entire procedure generally are controlled electronically. When sterilizing medical instruments, one cycle is often sufficient. The medical instruments are often packaged, with the entire package being placed into the sterilizing compartment. The package allows the hydrogen peroxide to penetrate and effect sterilization of the instruments, while subsequently protecting the instruments from contamination in air. The temperatures used in the process are all generally less than 65° C.

EXAMPLES

The invention will be illustrated in greater detail by the following specific examples. It is understood that these examples are given by way of illustration and are not meant to limit the disclosure or the claims to follow. All percentages in the examples, and elsewhere in the specification, are by weight unless otherwise specified.

TABLE 1

Materials

| Designation | Description | Source |
| --- | --- | --- |
| ABTS | (2,2'-Azino-bis(3-ethylbenzothiazoline-6-sulfonic acid)diammonium salt | Sigma Aldrich, St. Louis, MO |
| DSSA | 4,4'-Diamino-2,2'-stilbenedisulfonic acid | Tokyo Chemical Industry, |
| $CeO_2$ NP | Cerium (IV) oxide nanoparticle 10 wt. % aqueous dispersion, <25 nm. | Sigma Aldrich, St. Louis, MO |
| AEAPS | N-[3-(Trimethoxysilyl)propyl]ethylenediamine | Sigma Aldrich, St. Louis, MO |
| R-966 | An aliphatic urethane latex, available under the trade designation NEOREZ R-966 | DSM USA, Parsippany, NJ |
| UD-420 | A polyurethane, available under the trade designation BONDTHANE UD-420 | Bond Polymers International, Seabrook, NH |
| PZ-28 | A polyaziridine crosslinker available under the trade designation PZ-28 | PolyAziridine LLC, |
| XK-98 | An acrylic crosslinker emulsion polymer, available under the trade designation NEOCRYL XK-98 | DSM USA, Parsippany, NJ |
| ACRONAL 4569 | A styrene-acrylic binder, available under the trade | BASF, Florham Park, NJ |

TABLE 1-continued

Materials

| Designation | Description | Source |
|---|---|---|
| ACRONAL 3587 | designation ACRONAL 4569 A cross-linkable acrylic copolymer, available under the trade designation ACRONAL 3587 | BASF, Florham Park, NJ |
| Clear PET film | A clear 5 mil (130 micrometers) poly(ethylene terephthalate) film | 3M, St. Paul, MN |
| White PET film | A white 3 mil (76 micrometers) poly(ethylene terephthalate) film | 3M, St. Paul, MN |

Test Method—Hydrogen Peroxide Detection ("HPD Teat Method")

Samples (strips) of coated and dried PET films were tested in a STERRAD 100S hydrogen peroxide sterilizer (available from ASP, Irvine, CA), according to the manufacturer's instructions. The samples were examined for color change by visual observation, and the resulting colors were reported in the tables below.

Comparative Example 1A (CE-1A)—no Dye Added 10 g of water was added to 10 grams of XK-98 and mixed well. Added 0.8 gram of $CeO_2$ NP (cerium (IV) oxide nanoparticle aqueous dispersion 10 wt. % in water) to the mixture and allowed to mix for about 10 minutes. The resulting mixture was coated onto a white PET film with #16 Mayer bar, and then dried at 100° C. for 10 min. Samples were white due to the white background.

Comparative Example 1B (CE-1B)—No Indicator Compound Added

The procedure of CE-1A was repeated, except that R-966 was used in place of XK-98. Samples of CE-1A and CE-1B were tested according to the HPD test method, except using a STERRAD NX hydrogen peroxide sterilizer. No color change was observed fir either CE-1A or CE-1B. Both samples remained white without noticeable color change.

Comparative Example 2 (CE-2)—no $CeO_2$ Nanoparticles Added

Into a brown glass jar, 1 gram of DSSA and then the corresponding amount of water as shown in Table 2 was added. Subsequently, aliquots of 30 wt. % ammonia were added with stirring for 15 minutes at room temperature until the DSSA was completely dissolved. To this solution the AEAPS and R-966 were added and mixed for another 15 minutes. To this mixture was added 1 gram of polyaziridine crosslinker PZ-28 and mixed well. The resulting clear solution was coated on a PET film substrate with a #28 Mayer bar and dried at 130° C. far 2 minutes. Samples of the coated film were tested according to the Hydrogen Peroxide Exposure test method. The samples turned to a light orange color.

TABLE 2

| Material | Weight percent of mixture |
|---|---|
| DSSA | 1 |
| 30 wt. % ammonia | 2 |
| AEAPS | 2 |
| R-966 (32 wt. % solids) | 64.5 |
| PZ-28 | 1 |
| Water | 29.5 |
| Total | 100 |

Examples 1 to 7 (EX-1 to EX-7)

A 1 gram amount of DSSA was dissolved in 50 grams of 0.1 N sodium hydroxide solution. To this solution, 50 grams of one of ACRANOL 4569, ACRANOL 3587, XK-98, UD-420, or R-996 was added according to the Examples listed in Table 3. The mixture was magnetically stirred and 2 grams of $CeO_2$ NP (cerium oxide nanoparticle aqueous dispersion 10 wt. % in water) was mixed in. The resulting formulations were coated clear PET film and dried at 120° C. for 2 minutes. All of the samples were initially colorless. Upon testing in the Hydrogen Peroxide Detection (MED) test method, the sample were visually observed, and were found to have tuned various shades of orange, as summarized in Table 3.

TABLE 3

| | Amounts of materials, in grams | | | | | | |
|---|---|---|---|---|---|---|---|
| Material | EX-1 | EX-2 | EX-3 | EX-4 | EX-5 | EX-6 | EX-7 |
| DSSA | 1 | 1 | 1 | 1 | 1 | 1 | 1 |
| 10 wt. % $CeO_2$ NP | 4 | 4 | 4 | 4 | 1 | 2 | 4 |
| 0.1N NaOH | 50 | 50 | 50 | 50 | 50 | 50 | 50 |
| ACRANOL 4569 | 50 | 0 | 0 | 0 | 0 | 0 | 0 |
| ACRANOL 3587 | 0 | 50 | 0 | 0 | 0 | 0 | 0 |
| XK-98 | 0 | 0 | 50 | 0 | 0 | 0 | 0 |
| UD-420 | 0 | 0 | 0 | 50 | 0 | 0 | 0 |
| R-966 | 0 | 0 | 0 | 0 | 50 | 50 | 50 |
| Visually observed color from HPD test method | Dark Orange | Light Orange | Orange | Orange | Light Orange | Light Orange | Orange |

Examples 8 to 13 (EX-8 to EX-13)

Amounts of materials for these formulations were as listed in Table 4 (in grams). A 1 gram amount of either DSSA or ABTS was suspended in 20.5 grams of water and then dissolved in either 30 wt. % ammonia or 4N NaOH solution according to the amounts in Table 4. The mixture was magnetically stirred and 2 grams of $CeO_2NP$ (cerium oxide nanoparticle aqueous dispersion 10 wt. % in water) was mixed in. To the resulting mixture was added 25 grams either UD-420 or R-996 (see Table 4). The resulting formulations were coated onto clear PET film and then dried at 120° C. for 2 minutes. All of the samples were initially colorless. Upon testing in the Hydrogen Peroxide Detection (HPD) test method, the samples were visually observed and found to exhibit the colors as summarized in Table 4.

TABLE 4

Amounts of materials, in grams

| Material | EX-8 | EX-9 | EX-10 | EX-11 | EX-12 | EX-13 |
|---|---|---|---|---|---|---|
| DSSA | 1 | 1 | 0 | 0 | 1 | 1 |
| ABTS | 0 | 0 | 1 | 1 | 0 | 0 |
| Water | 20.5 | 20.5 | 20.5 | 20.5 | 20.5 | 20.5 |
| 30 wt. % ammonia | 2.5 | 2.5 | 2.5 | 2.5 | 0 | 0 |
| 4N NaOH | 0 | 0 | 0 | 0 | 1.5 | 1.5 |
| 10 wt.% $CeO_2$ NP | 2 | 2 | 2 | 2 | 2 | 2 |
| R-966 | 25 | 0 | 25 | 0 | 25 | 0 |
| UD-420 | 0 | 25 | 0 | 25 | 0 | 25 |
| Visually | Blood orange | Dark orange | Green | Green | Orange | Dark orange |

Examples 14 to 16 (EX-14 to EX-16)

Amounts of materials far these formulations were as listed in Table 5 (in grams). A 0.5 gram amount of DSSA was suspended in 19.3 grams of water and then dissolved in 2.7 grams of IN NaOH solution. To the solution was added 25 grams of one of R-966, LTD-420, or XK-98 (see Table 5). The mixture was magnetically stirred and 2 grams of 110 wt. % cerium oxide nanoparticle suspension was mixed in. To the resulting mixture was added either UD-420 or R-996, again according to Table 5 The resulting formulations were coated clear PET film and dried at 120° C. for 2 minutes. All of the samples were initially colorless. Upon testing in the Hydrogen Peroxide Detection (HPD) test method, the sample were visually observed, and were found to exhibit the colors as summarized in Table 5.

TABLE 5

Amounts of materials, in grams

| Material | EX-14 | EX-15 | EX-16 |
|---|---|---|---|
| DSSA | 0.5 | 0.5 | 0.5 |
| 10 wt. % $CeO_2$ NP | 2 | 2 | 2 |
| 1N NaOH | 2.7 | 2.7 | 2.7 |
| R-966 | 25 | 0 | 0 |
| UD-420 | 0 | 25 | 0 |
| XK-98 | 0 | 0 | 25 |
| Visually observed color from HPD test method | Dark orange | Orange | Blood orange |

Examples 17 to 19 Laminate Articles with Diffusion Through a Channel

A coated clear PET sample from EX-16 (which included XK-98) was cut into 2 inch (5.1 cm) wide strips and the sample strips were laminated between two layer of clear 3 mil (76 micrometer) PET film. A control sample was laminated on only one side. A channel between one or both ends of the sample strips was created by including 5 mil (about 130 micrometers) of PET film between the outer PET film layer to create laminates having a 5 mm wide channel with openings on one end, both ends, or neither end, according to Table 6. The sample articles were subjected to the HPD test method, with results as summarized in Table 6.

TABLE 6

| | Control | EX-17 | EX-18 | EX-19 |
|---|---|---|---|---|
| PET laminate | Only one side | Both sides | Both sides | Both sides |
| Channel openings | Not applicable | Neither end | One end | Both ends |
| HPD test result | Blood orange on entire exposed surface | No evidence of color development | Blood orange at open end only | Blood orange at both ends |

While embodiments of the invention have been described, it will be appreciated that changes and modifications may be made to the various features of the embodiments described herein without departing from the spirit and scope of the invention.

What is claimed is:

1. An indicator article for detecting hydrogen peroxide, comprising
    a substrate and an indicator composition deposited thereon, wherein the indicator composition comprises:
        at least one indicator compound comprising 4,4'-diamino-2,2'-stilbenedisulfonic acid (DSSA); and
        a catalyst comprising cerium (IV) oxide nanoparticles;
    wherein the indicator composition comprises an optical property,
    wherein a visually detectable change in the optical property of the indicator composition is associated with a presence of hydrogen peroxide.

2. The indicator article of claim 1, wherein the cerium (IV) oxide nanoparticles are present in a range from 0.0001 wt. % to 20 wt. % of the indicator composition.

3. The indicator article of claim 1, wherein the cerium (IV) oxide nanoparticles are present in a range from 0.005 wt. % to 1 wt. % of the indicator composition.

4. The indicator article of claim 1, wherein the catalyst accelerates a color change of the indicator composition.

5. The indicator article of claim 1, wherein the indicator compound is colorless by visual observation when dissolved in water at a concentration of up to 0.1 wt. %, prior to exposure to hydrogen peroxide vapor.

6. The indicator article of claim 1, wherein the hydrogen peroxide is in a sterilant vapor.

7. The indicator article of claim 1, wherein the change in the optical property of the indicator composition is a change from having no visually detectable color to having a visually detectable color.

8. The indicator article of claim 1, wherein the indicator composition further comprises a polymeric binder and/or a crosslinker.

9. The indicator article of claim 1, wherein the substrate is a polyester film.

10. A method comprising:
    providing the indicator article of claim 1, comprising the indicator composition;

exposing the indicator composition to hydrogen peroxide vapor;

and visually detecting a change in an optical property of the indicator composition upon exposure to the hydrogen peroxide vapor.

11. The method of claim 10, wherein the change in the optical property of the indicator composition is a change from colorless to having a visually detectable color.

* * * * *